United States Patent
Jono et al.

(10) Patent No.: US 8,660,389 B2
(45) Date of Patent: Feb. 25, 2014

(54) OPTICAL CONNECTOR AND OPTICAL TOMOGRAPHIC IMAGING APPARATUS

(75) Inventors: Junichi Jono, Hachioji (JP); Katsumi Fujiwara, Hachioji (JP); Fumio Nagai, Kunitachi (JP)

(73) Assignee: Konica Minolta Opto, Inc., Tokyo (JP)

(*) Notice: Subject to any disclaimer, the term of this patent is extended or adjusted under 35 U.S.C. 154(b) by 150 days.

(21) Appl. No.: 13/322,149

(22) PCT Filed: Mar. 5, 2010

(86) PCT No.: PCT/JP2010/053639
§ 371 (c)(1),
(2), (4) Date: Nov. 22, 2011

(87) PCT Pub. No.: WO2010/137375
PCT Pub. Date: Dec. 2, 2010

(65) Prior Publication Data
US 2012/0069348 A1    Mar. 22, 2012

(30) Foreign Application Priority Data
May 28, 2009    (JP) .................................. 2009-128811

(51) Int. Cl.
*G02B 6/26*    (2006.01)

(52) U.S. Cl.
USPC ............................................. 385/26; 385/31

(58) Field of Classification Search
USPC .......................................................... 385/26
See application file for complete search history.

(56) References Cited

U.S. PATENT DOCUMENTS

| 9,493,929 | 9/1999 | Hamm |
| 6,687,010 B1 | 2/2004 | Horii et al. |
| 2011/0164255 A1* | 7/2011 | Konno et al. .................. 356/479 |

FOREIGN PATENT DOCUMENTS

| JP | 3-100807 | 10/1991 |
| JP | 6-511312 | 12/1994 |
| JP | 11-148897 | 6/1999 |
| JP | 2000-321034 | 11/2000 |
| JP | 2001-507251 | 6/2001 |
| JP | 2005-533533 | 11/2005 |
| JP | 2008-183343 | 8/2008 |
| WO | WO 92/19930 | 11/1992 |

OTHER PUBLICATIONS

Full English Translation of JP 03-100807, obtained Sep. 2013.*

* cited by examiner

*Primary Examiner* — Omar Rojas
(74) *Attorney, Agent, or Firm* — Cozen O'Connor (57) ABSTRACT

Provided are an optical connector and an optical tomographic imaging apparatus, by which no noise occurs and a high quality image without a distortion can be obtained. In the optical connector, optical fibers are inserted into a lumen of a tube from opposite ends thereof; one of the optical fibers is fixed to the tube and the other optical fiber is held so as to be rotatable relative to the tube; an end of one of the optical fibers is separated from an end of the other optical fiber to form a gap therebetween in the lumen; a connecting section which connects the exterior space of the tube and the gap is formed; and a liquid or fluid made of a material which can transmit light is held in the exterior space, the gap, and the connecting section. Consequently, a significant pressure variation in matching liquid does not occur if the distance between the facing optical fibers changes.

7 Claims, 6 Drawing Sheets

OPTICAL CONNECTOR AND OPTICAL TOMOGRAPHIC IMAGING APPARATUS

RELATED APPLICATIONS

This application is a U.S. National Phase Application under 35 USC 371 of International Application PCT/JP 2010/053639 filed Mar. 5, 2010.

This application claims the priority of Japanese application No. 2009-128811 filed May 28, 2009, the entire content of which is hereby incorporated by reference.

TECHNICAL FIELD

The present invention relates to an optical connector and an optical tomographic imaging apparatus.

BACKGROUND ART

A method to taking a tomograpic image of human tissue noninvasively by using low coherent interference is known (for example, Patent Literature 1). In the tomograpic imaging, low coherence light emitted from a light source is divided into irradiation light and reference light. The irradiation light is irradiated to human tissues through a light guide. On the other hand, the reference light enters a movable mirror in an optical path length adjusting section. After that, the irradiation light (scattered light) reflected by respective tissues of a human body and the reference light reflected by the movable mirror are combined, and reference light having the same optical path length as the optical path length of the reference light is participate in interference at that place. Accordingly, by analyzing the intensity of interfering light, there can be obtained a tomographic image of tissues corresponding to scattered light having the optical path length which is the same as the optical path length of the reference light. By using the theory of the optical tomography, a tomographic image of tissues which spread in a broad area can be obtained. For example, an optical fiber wherein a rectangular prism is arranged on its leading end is inserted in a blood vessel, and the optical path length of the reference light is changed corresponding to the tomographic imaging position while scanning is carried out with the irradiation light in the circumference direction by rotating the optical fiber on the longitudinal axis. Thereby, a tomographic image of a blood vessel can be obtained.

As described above, in the optical tomography in which scanning is carried out with the irradiation light in the circumference direction, a light guide tube for guiding the irradiation light which has been separated from the reference light is composed of, for example, an optical fiber (non-rotating optical fiber) which guides the irradiated light which has been separated and a second optical fiber (rotary scanning optical fiber) which receives the irradiated light from the former optical fiber to guide the light to the rectangular prism at the leading end and rotates on the longitudinal axis. In this case, it is required that the first optical fiber and the second optical fiber are optically connected together with the second optical fiber being rotatable with respect to the first optical fiber.

Patent Literature 2 discloses an optical connector which meets the above demands. The optical connector of Patent Literature 2 employs a structure that plural optical lenses are arranged between the end section of the first optical fiber and the end section of the second optical fiber and light emitted from one of the end section of the optical fibers is converged by the lenses to enter into the other end section of the optical fibers. However, as for the optical connector, it is required that small lenses are mounted in a small area with accuracy.

Another optical connector which solves the defect of the lens-type connector disclosed in Patent Literature 2, is disclosed, for example, in Patent Literature 3. The optical connector disclosed i„ Patent Literature 3 connects the ends of the first and second optical fibers by closing the ends in a narrow space in a tube shape, whereby the ends are optically connected without using lenses. Refractive-index matching liquid is deposited in the gap between the ends to reduce Fresnel reflection that light is reflected on the end surfaces of the optical fibers.

However, a rotating optical fiber oscillates in the longitudinal direction corresponding to its rotation, which changes the distance of the opposite surfaces of the two optical fibers. This change in distance is propagated to the matching liquid filling the space between the optical fibers, which causes a change of the liquid in pressure and changes of the liquid in density and refractive index coming from the change in pressure. The change in refractive index brings generation of noise and distortion of the tomographic image, which are problems.

Further, when negative pressure is applied to the matching liquid, bubbles are generated or flows in the matching liquid and the light propagating efficiency is significantly reduced because the bubbles block an optical path. Concretely, in the case of a single-mode optical fiber, the outer diameter of a clad is about 125 μm and the pressure of the matching liquid considerably changes when the interval of the two optical fibers changes by only 1 mm in the direction of the longitudinal axis, which can make bubbles easily. The generation of bubbles causes the problem that a tomograpic image cannot be formed.

CITATION LIST

Patent Literature

Patent document 1: Japanese Translation of PCT International Application Publication No. H06-511312
Patent document 2: U.S. Pat. No. 6,687,010
Patent document 3: U.S. Pat. No. 5,949,929

SUMMARY OF INVENTION

Technical Problem

In view of the above problems, the present invention is aimed at providing an optical connector and optical tomographic imaging apparatus which do not generate noise and enable to obtain an excellent tomograpic image without distortion.

Solution to Problem

An optical connector described in item 1 is an optical connector comprising a tube, wherein optical fibers are inserted into a lumen of the tube from both sides of the tube, one of the optical fibers is held in a non-rotating condition relatively to the tube, the other of the optical fibers is held in a rotatable condition relatively to the tube, an end of one of the optical fiber and an end of the other of the optical fiber are separated in the lumen to form a gap between the ends, and one of the optical fibers and the other of the optical fibers are optically connected through the gap. The optical connector is characterized by further comprising a connecting section for connecting an exterior space of the tube and the gap, wherein the exterior space, the gap and the connecting section hold liquid or fluid composed of a material which can transmit light.

An optical connector described in item 2 is the optical connector of item 1, characterized in that the connecting section is formed in at least one of the tube, the one of the optical fibers and the other of the optical fibers.

An optical connector described in item 3 is the optical connector of item 1 or 2, characterized by further comprising: a stator stationarily arranged so as not to rotate; and a rotator supported so as to be rotatable on a center axis of the tube relatively to the stator, wherein the exterior space is formed with the stator and the rotator, and an end section of the one of the optical fiber or the other optical fiber is fixed to the rotator.

An optical connector described in item 4 is the optical connector of item 3, characterized in that the tube is fixed to the rotator.

An optical connector described in item 5 is the optical connector of item 3, characterized in that the tube is fixed to the stator.

An optical connector described in item 6 is the optical connector of item 1, characterized in the connecting section is formed in a tube member arranged between at least one of the one of the optical fiber and the other of the optical fiber, and the tube.

An optical tomographic imaging apparatus described in item 7 is provided for obtaining a tomographic image of a subject by a way that light emitted from a light source is divided into irradiation light and reference light, the irradiation light is guided with an optical fiber, and interfering light of the irradiation light and the reference light is detected while the subject is irradiated with the irradiation light along a transverse cross section of the subject by rotating the optical fiber on a longitudinal axis thereof under a condition that the optical fiber is inserted to the subject. The optical tomographic imaging apparatus is characterized in that an optical fiber to be inserted to the subject is optically connected with the optical connector of any one of items 1 to 6, and the irradiation light is transmitted through the optical connector and the optical fiber to be inserted to the subject.

Advantageous Effect of the Invention

According to the present invention, an optical connector and optical tomographic imaging apparatus which do not generate noise and enable to obtain an excellent tomograpic image without distortion can be provided.

DESCRIPTION OF EMBODIMENTS

Hereinafter, embodiments of an optical tomograpic imaging apparatus and an optical connector relating to the present invention will be described referring with appended drawings.

Figure 1:
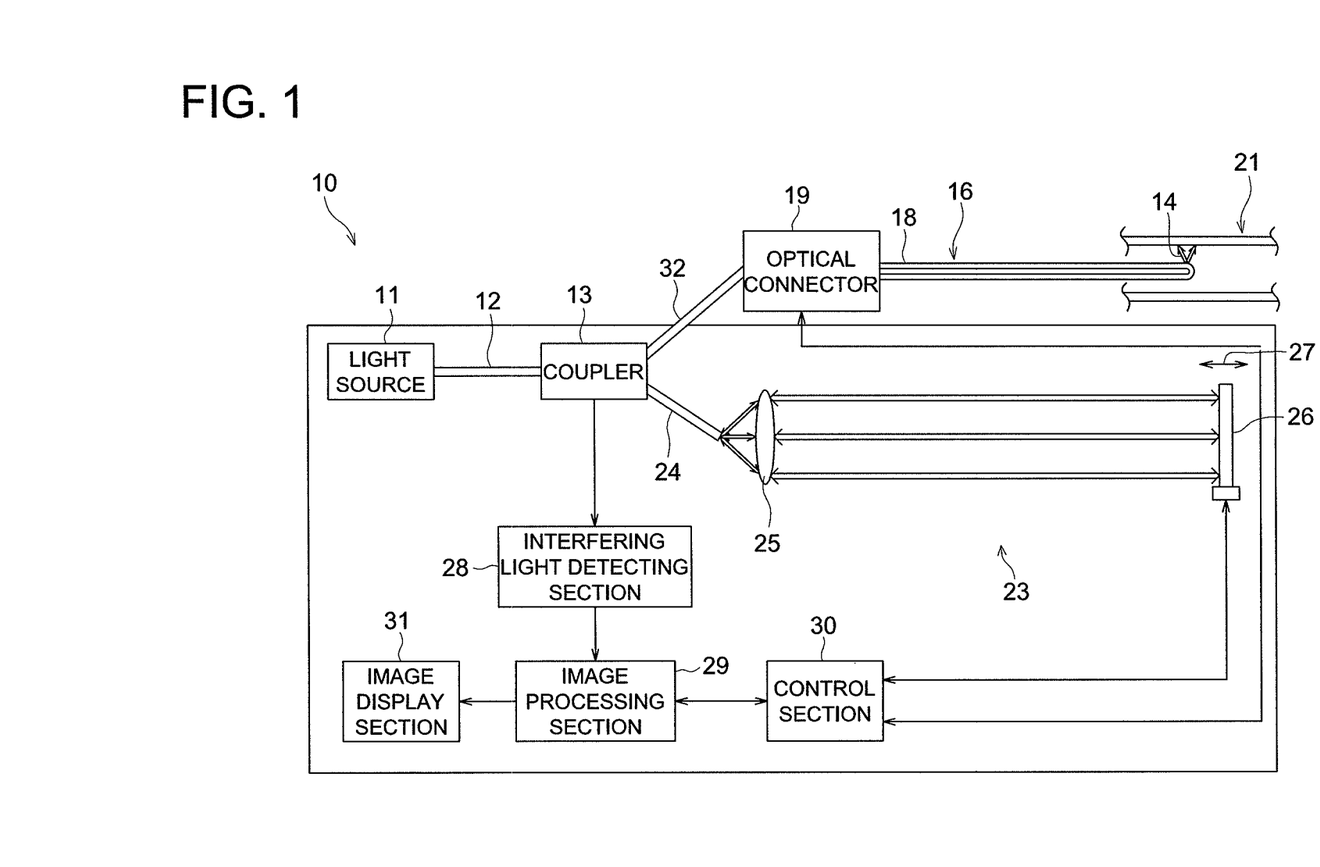
FIG. 1 is a diagram showing a structure of an optical tomograpic imaging apparatus relating to the present embodiment
Figure 2:
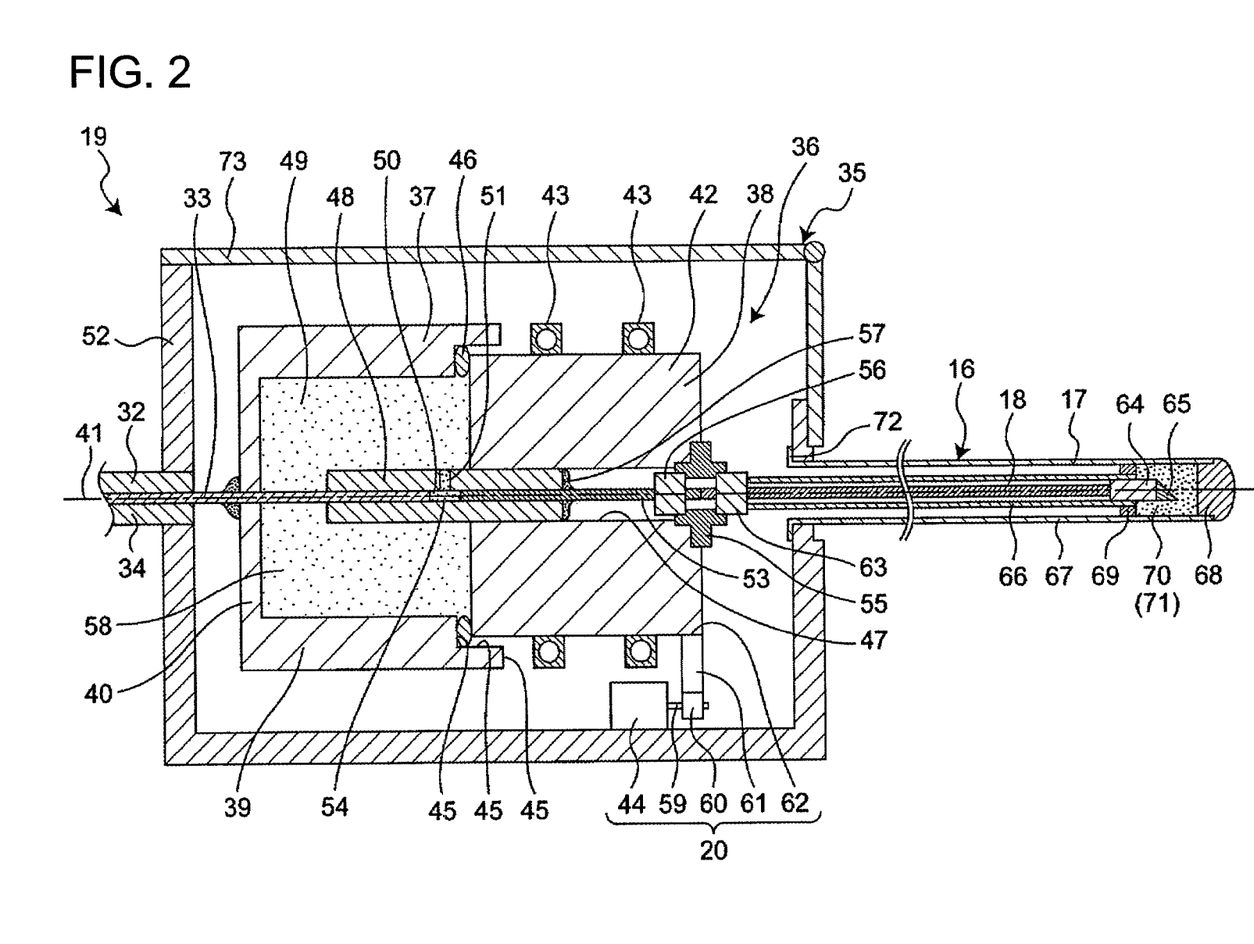
FIG. 2 is a sectional view of an optical connector with which an optical tomograpic imaging apparatus relating to the present embodiment is equipped.

FIG. 1 is a diagram showing a structure of an optical tomograpic imaging apparatus 10 relating to the present embodiment. FIG. 2 is a sectional view of an optical connector with which the optical tomograpic imaging apparatus relating to the present embodiment is equipped.

In FIG. 1, light source 11 emits low coherence light 12 in a imaging process. The wavelength of low coherence light 12 is in the range from 0.7 μm to 2.5 μm. As a light source generating low coherence light 12, a super luminescent diode (SLD) is suitably employed.

Low coherence light 12 emitted from light source 11 enters coupler 13. Therefore, light source 11 and coupler 13 are optically connected with an optical fiber, a lens optical system, or a combination of them.

Coupler 13 divides the emitted low coherence light 12 into two types of light: irradiation light and reference light. The irradiation light which is one of the divided two types of light is guided to probe 17 (see FIG. 2) of irradiation section 16. As shown in FIG. 2, probe 17 houses optical fiber 18 therein. The proximal end of optical fiber 18 (the left-side end in FIG. 2) is connected with optical connector 19 to be rotatable on the longitudinal axis. Optical connector 19 includes a rotator and rotation mechanism 20 (which is not illustrated) for rotating the rotator, to enable to rotate optical fiber 18 on the longitudinal axis based on the drive of rotation mechanism 20, which will be described later. On the other hand, on the distal end of optical fiber 18, there is arranged an optical component (for example, a rectangular prism, which will be described later) for deflecting the propagating direction of irradiation light which is transmitted through the optical fiber 18 from its proximal end, to the radial direction of probe 17. Therefore, irradiation light supplied to probe 17 is transmitted to the distal end of the probe through optical fiber 18, and is emitted from there to the outside in the radial direction through rectangular prism 65, and the imaging subject is irradiated with the reference light. The irradiation light moves in the circumference direction corresponding to the rotation of optical fiber 18.

The imaging subject is, for example, a blood vessel 21. In this case, the distal end of optical fiber 18 is inserted into blood vessel 21, and emits irradiation light through rectangular prism 65 at the distal end to the outside in the radial direction, which is from the inside to the outside of blood vessel 21. Further, optical fiber 18 rotates on the longitudinal axis. Thereby, the blood vessel and its surrounding tissues are scanned by the irradiation light. Then, light (scattered light) which has been scattered in the inner wall of the blood vessel and inner tissues is taken into rectangular prism 65 on optical fiber 18 and is transmitted to coupler 13. Herein, the imaging subject is not limited to a blood vessel.

As shown in FIG. 1, the reference light which is the other of two types of light divided by coupler 13 is guided to optical path length adjusting section 23. Optical path length adjusting section 23 converts, for example, the reference light transmitted from coupler 13 through light guide 24 (for example, an optical fiber) into parallel light by lens optical system 25. The converted parallel light is reflected by mirror 26 and returns to coupler 13 through optical system 25 and light guide 24. Mirror 26 is supported by moving mechanism 27 which goes forward and back with respect to lens optical system 25. By moving mirror 26 based on the drive of moving mechanism 27, optical path length (optical distance) of the reference light can be changed.

The scattered light and the reference light which have returned to coupler 13 is combined together, and are sent to interfering light detecting section 28. In other words, coupler 13 works as a light dividing means and a light combining means.

Interfering light detecting section 28 acquires intensity information of interfering light of the scattered light and reference light which have been combined and transmits the information to image processing section 29. Image processing section 29 receives the intensity information of the interfering light from interfering light detecting section 28 and acquires control information from control section 30.

Control section 30 caries out synchronizing control for the movement of mirror 26 and the rotation of optical fiber 18. Concretely, control section 30 drives moving mechanism 27 based on the information of an optical path length generated in control section 30 to move movable mirror 26 forward or backward with respect to optical system 25, which changes the optical path length of the reference light. Further, control section 30 drives rotation mechanism 20 and rotates optical fiber 18, to scan a blood vessel along its transverse section with the irradiation light. At that time, control section 30 acquires rotation angle (rotation angle information) of optical fiber 18, where the rotation angle is outputted from rotating mechanism 20. Then, control section 30 outputs information of the rotation angle of optical fiber 18 and information of the optical path length of the reference light, to image processing section 29. Image processing section 29 processes the intensity information of the interfering light based on the information of the optical path length and forms a tomographic image of the blood vessel. The formed tomographic image is displayed by image display section 31.

In the process forming the tomographic image, by rotating optical fiber 18 under the condition that mirror 26 is located a certain position, annular sectional image of tissues located at a predetermined distance from the rotation center of the optical fiber can be obtained. Further, by rotating optical fiber 18 under the condition that the optical path length is changed by moving mirror 26 from the above condition, annular sectional image of tissues located at the position which moves to be deeper than the predetermined position can be obtained. As described above, when the irradiation light moves along the circumference direction based on the rotation of optical fiber 18, while the optical path length of the reference light is changed by the movement of the movable mirror 26, a tomographic image coveting the entire of the transverse section of the blood vessel can be obtained. Further, when probe 17 rotates plural times under the condition that movable mirror 26 is located at a predetermined position, plural images of the same annular cross section can be obtained and an excellent tomographic image can be obtained by averaging the images.

Further, the detail of the structure of irradiation section 16 will be described referring with FIG. 2. As shown in the figure, irradiation section 16 includes light guide tube 32 for guiding the irradiation light emitted from coupler 13 to optical connector 19, additionally to probe 17 and optical connector 19. Light guide tube 32 includes optical fiber 33 and jacket 34 covering the outer circumference of the optical fiber 33, and the two ends of tube 32 are connected to coupler 13 and optical connector 19, respectively.

Optical connector 19 includes housing 35. As shown in the figure, housing 35 of the present example is composed of a container in a boxed shape. Rotary joint 36 is housed inside housing 35. Rotary joint 36 includes stator (stationary section) 37 and rotator (rotation section) 38. Stator 37 includes annular tube section 39 and end wall 40 for closing the proximal end (the left side of the figure) of annular tube section 39 which are formed in one body. Stator is fixed on housing 35 under the condition that the center axis of annular tube section 39 agrees with the base axis (rotation axis) 41.

Rotator 32 is composed of cylinder 42 and is supported by bearing 43 arranged on housing 35 so as to be rotatable on base axis 41 under the condition that the center axis of cylinder 42 agrees with base axis 41. Cylinder 42 is connected with motor 44 of rotation mechanism 20 arranged on housing 35 so as to be driven, and is configured to rotate on base axis 41 based on the rotation of motor 44. As for stator 37 and rotator 38, the proximal end of rotator 38 (the left side of the figure) is fitted into inner step section 45 formed on the distal end (the right side of the figure) of stationary annular tube section 39, and a space between stator 37 and rotator 38 is sealed with proper sealing 46. In the example, seal 46 is fixed on stator 37. Seal 46 is preferably formed by oil seal. However, seal 46 is not limited to the oil seal and can be other seals such as metal seal. Alternatively, seal 46 is preferably formed of a material with strength and elasticity such as fluororubber.

At the center of rotator 38 composed of cylinder 42, through hole 47 is formed along base axis 41, and capillary tube 48 is fixed therein. As it is illustrated, capillary tube 48 has the almost same outer diameter as the inner diameter of through hole 47. The distal end of the capillary tube at the right hand side of the figure is inserted into the proximal end of through hole 47 to be fixed, and the proximal end of the capillary tube at the left hand side of the figure protrudes into chamber 49 which is an interior space of stationary annular tube section 39.

Capillary tube 48 includes cavity (lumen) 50 with a small diameter penetrating capillary tube 48 along base axis 41. The inner diameter of cavity 50 is almost same as the outer diameters of the dads of the optical fibers to be used in the present example. Capillary tube 48 further includes connecting section 51 with a small diameter which connects cavity 50 and chamber 49 of stationary annular tube section 39. In the example, connecting section 51 is formed as a hole with small diameter.

The size of capillary tube 48 is 2 mm in outer diameter and 20 mm in length. The size of cavity 50 depends on conditions for use. Concretely, optical fibers are separately inserted into the both sides of cavity 50 of capillary tube 48, which will be described below, and these optical fibers are optically connected at their opposing end sections. Therefore, the inner diameter of cavity 50 is set to be the same as or slightly lager than the outer diameters of the clads of the optical fibers to be used. For example, when the diameter (which is the value including tolerance) of the dads of the optical fibers is 125 to 126 μm, the inner diameter of cavity 50 is set to be 126 μm. Accordingly, when the tolerance of the outer diameters of the dads is zero, the opposing two optical fibers can shift by at most 1 pm in cavity 50. However, the diameter of the cores of the optical fibers are about 10 μm generally, and the shift amount of the axes is as small as about 10% of the core diameter. Therefore, two optical fibers can be connected in an excellent condition.

Capillary tube 48 is desired to have the feature that optical fibers can be easily inserted into cavity 50, to enable to be processed with high accuracy (to enable to ensure a desired straightness for the cavity and to obtain the desired concentricity between the cavity and the outer circumference surface), and to have a desired toughness, an excellent anti-impact property, and coefficient of thermal expansion which is close to that of the optical fibers (in order to prevent the relative movement of the capillary tube and the optical fiber). Therefore, capillary tube 48 is preferably formed of sintered ceramic. In order to minimize the insertion resistance of the optical fibers, the capillary tube is preferably formed of glass.

Optical fiber 33 of light guide tube 32 is connected with the capillary tube 48. Concretely, the distal end of light guide tube 32 disposed at the side of the proximal end penetrates wall 52 of housing 35 along base axis 41, and is fixed on wall 52 with an unillustrated fixing means (for example, adhesive). Inside housing 35, a coat of light guide tube 32 is removed and optical fiber 33 is exposed. This optical fiber 33 penetrates end wall 40 of stator 37, and enters cavity 50 of capillary tube 48 through chamber 49. The distal end of optical fiber 33 is positioned at the side of the proximal end of connecting section 51.

The proximal end of optical fiber 53 is inserted in cavity (lumen) 50 of capillary tube 48, from the distal end of the cavity. The proximal end of optical fiber 53 is located at the side of the distal end of the connecting section 51. Therefore, the distal end of optical fiber 33 and the proximal end of optical fiber 53 face across connecting section 51, and gap 54 is formed between them. For example, the length of gap 54 in the direction of the rotation axis is adjusted within about 0.1 mm. Thereby, optical fibers 33 and 53 are concentrically arranged along base axis 41 and are optically connected with each other. The distal end of optical fiber 53 is connected with adapter 55 which is fixed to the opening section at the distal end of through hole 47 through connector 56. Then, optical fiber 53 is fixed to capillary tube 48 with adhesive arranged on the distal end of capillary tube 48. At the same time, capillary tube 48 is fixed to rotator 38 with the adhesive 57.

Chamber 49 which is tightly sealed by combining stator 37 and rotator 38, is filled with matching material 58. Matching material 58 is preferably a material which can transmit irradiation light and scattered light without attenuating them as much as possible. For matching material 58, liquid or fluid (gel material) with a refractive index being almost the same as those of the cores of the optical fibers 33 and 53 is used. Thereby, Fresnel reflection on the core ends of optical fibers 33 and 53 is reduced and attenuation of propagating light is controlled. The filling process of matching material 58 can be carried out through a filling hole (which is not illustrated) arranged on annular tube section 39 or end wall 40 of stator 37. Matching material 58 which has filled up chamber 49 enters gap 54 from connecting section 51 and exists between opposing optical fibers 33 and 53.

Accordingly, transparent matching material 58 is stored in chamber 49 which is an exterior space of capillary tube 48, gap 49, and connecting section 51.

Rotation mechanism 20 for rotating rotator 38 includes motor 44. As described above, motor 44 is electrically connected with control section 30 and rotates based on the rotation control signal outputted from control section 30. Therefore, gear 60 is fixed to rotation shaft 59 of motor 44. Gear 60 meshes with another gear 61. Gear 61 further meshes with gear 62 formed on the outer circumference surface of cylinder 42 as a rotator. Accordingly, rotator 38 rotates corresponding to a drive operation of motor 44. The means to transmit the rotation of motor 44 to rotator 38 is not limited to a gear mechanism, and may be a structure that a belt and pulley are combined. Further, the type of motor 44 is not limited, but a stepping motor is preferably used for motor 44 in order to synchronize the rotation of rotator 38 and the movement of mirror 26 as described above.

Probe 17 to be connected with rotary joint 36 which is structured as above, includes optical fiber 18 as described above. Connector 63 is connected with the proximal end of optical fiber 18. Connector 63 can be connected with adaptor 55 of rotary joint 36 such that the connector can be attached to or detached from the adapter 55 freely, and optically connects optical fiber 18 and optical fiber 53 under the condition that the connector is connected with adaptor 55. Therefore, for connectors 56 and 63 and adapter 55, a FC connector and FC adapter, or a SC connector and SC adapter which are suitable to connection of optical fibers are preferably used.

On the distal end of optical fiber 18, distributed (gradient) index lens (hereinafter, referred as "lens") 64 and rectangular prism 65 for deflecting a propagating direction of the irradiation light emitted from lens 64 to the radial direction of probe 17 are fixed. A mirror section formed of a metal film for reflecting the irradiation light is formed on the sloped surface of the rectangular prism 65. Optical fiber 18 is externally wrapped with torque transmitting sleeve 66 for transmitting the rotation of rotator 38 to lens 64 at the distal end. Sleeve 66 has a flexibility which is required to ensure a free movement of the optical fibers. Therefore, sleeve 66 is preferably formed of a torque wire or a spring wire each in a tube shape formed by spirally winding thin wires.

Almost all of the optical fiber 18 protruding from housing 35 is covered with sheath 67. Sheath 67 is formed of a transparent flexible material (for example, polytetrafluoroethylene). The distal end of the sheath extends past rectangular prism 65 and an opening of the distal end is sealed with cap 68. Further, sealing member 69 formed of a rubber ring is arranged between a portion of sleeve 66 where sleeve 66 is connected with lens 64 or an exposed outer circumference surface of sleeve 66, and a sheath section facing it. Space 70 formed between cap 68 and sealing member 69 is filled with matching material 71 having a refractive index being almost the same as or close to the refractive index of rectangular prism 65. Thereby, Fresnel reflection is reduced on the outgoing surface and incident surface of prism 65, and attenuation of the propagating light is controlled. The proximal end of sheath 67 is located at a position closer to the distal end side than the proximal end of optical fiber 18, and ring-shaped clamp 72 is fixed thereon.

Probe 17 formed as above is inserted into the through hole formed on wall 52 of housing 3 as it is illustrated. Connector 63 is connected to adaptor 55, and clamp 72 is fixed around through hole 47, and the probe is connected to optical connector 19. In order to carry out this operation easily, a part of housing 53 is formed as flap 73 which can be opened and closed, and the above connecting operation is carried out with flap 73 being opened. It is naturally understood that probe 17 can be detached and be replaced with another component by separating connector 63 from adaptor 55 and bringing clamp 72 from housing 35.

The movement of irradiation section 16 structured as described above will be described. In the above tomographic imaging process, motor 44 is driven based on the signal outputted from control section 30 and rotates rotator 38. Due to the rotation, optical fiber 53 which is fixed inside rotator 38 and optical fiber 18 which is connected to capillary tube 48 and rotator 38 and is located inside probe 17 rotate on base axis 41. The irradiation light which is divided with coupler 13 passes optical fiber 33 covered with light guide tube 32, optical fiber 53 fixed inside rotator 38, and optical fiber 18 housed in probe 17, and is transmitted to lens 64 and rectangular prism 65. Then, the light is reflected by a metal-film mirror formed on the sloped surface of rectangular prism 65 and is emitted outside in the radial direction of probe 17 and is projected outside in the radial direction through matching material 71 and transparent sheath 67. The irradiation light which has been projected is moved in the circumference direction with the rotation of optical fiber 18.

For example, in the case of the above-described tomographic imaging of a blood vessel, the projected irradiation light is scattered on the inner wall and inner tissues of blood vessel 21. A part of the scattered light enters an incident surface of rectangular prism 65 through sheath 67 and matching material 71, passes through lens 64, rotating optical fibers 18 and 53 and fixed optical fiber 33, and returns to coupler 13.

Under the rotation of rotator 38, the distance of fixed optical fiber 38 and rotating optical fiber 53 changes because of vibration caused by the rotation. Even when the change amount of the distance is very small (for example, 1 mm), the inner diameter of cavity 50 is very small (125 to 126 μm) and a change in pressure inside gap 54 becomes extremely large under the condition that the matching material is stored only in gap 54. However, as described above, gap 54 is connected with exterior chamber 49 through connecting section 51, which allows that matching material 58 in chamber 49 goes in and out gap 54 corresponding to the pressure change in gap 54 and the pressure in gap 54 is maintained to be almost constant.

In other words, by providing a structure wherein transparent matching material 58 is stored in chamber 49 as an exterior space of capillary tube 48, gap 54 and connecting section 51, large pressure change is not caused in the matching liquid in the gap 54 even when the gap of opposing optical fibers 33 and 53 changes because of the rotation. It solves the problem that negative pressure is applied to the matching material 58 filling gap 54 and changes in density and refractive index and generation of bubbles are caused in the matching material 58 which fills gap 54. Further, it enables to provide an optical connector and optical tomographic imaging apparatus which generates less noise and enables to obtain an excellent tomographic image without distortion.

The above-described optical tomographic imaging apparatus and optical connector are not limited to the above embodiment and can be modified in various embodiments.

Figure 3:
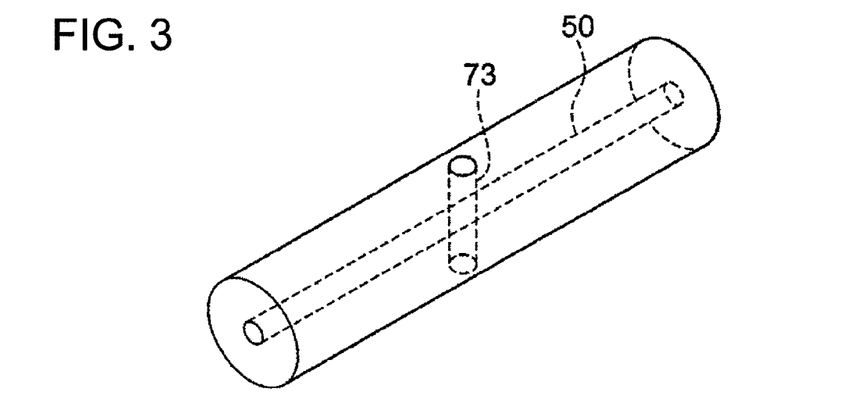
FIG. 3 is a perspective view showing the first modified example of a capillary tube.

For example, in the above embodiment, connecting section 51 is formed as a hole extending from cavity 50 toward the outside in the radial direction in a one-way manner. However, it may be formed as plural holes 73 extending in two or more directions (for example, in opposite directions) toward the outside in the radial direction, as shown in FIG. 3.

Figure 4:
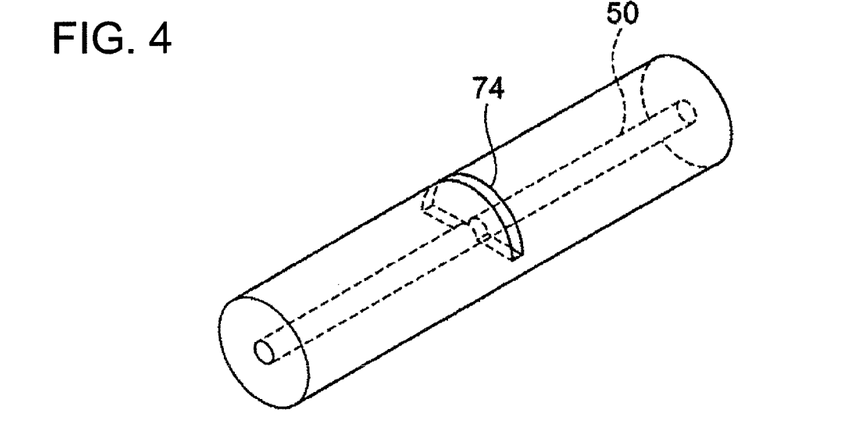
FIG. 4 is a perspective view showing the second modified example of a capillary tube.

Connecting section 51 is not needed to be a hole, and can be groove 74 which extends across cavity 50 as shown in FIG. 4.

Figure 5:
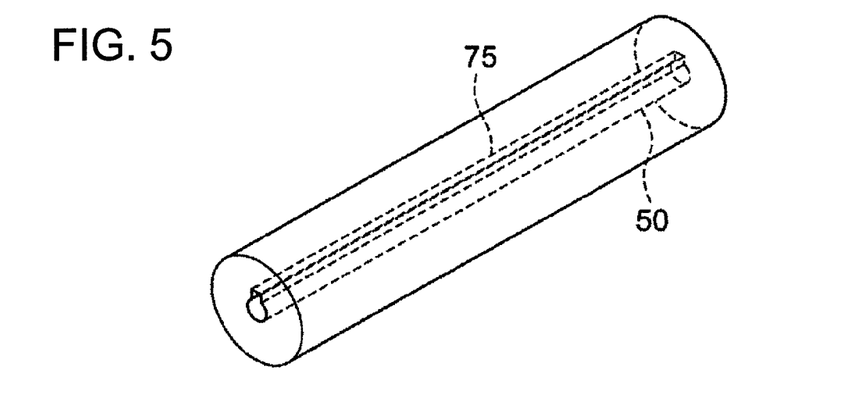
FIG. 5 is a perspective view showing the third modified example of a capillary tube.

Connecting section 51 is not needed to be a hole and groove extending in the radial direction, and can be connecting groove 75 forming a straight line or a spiral along the inner surface of cavity 50 as shown in FIG. 5.

Figure 6:
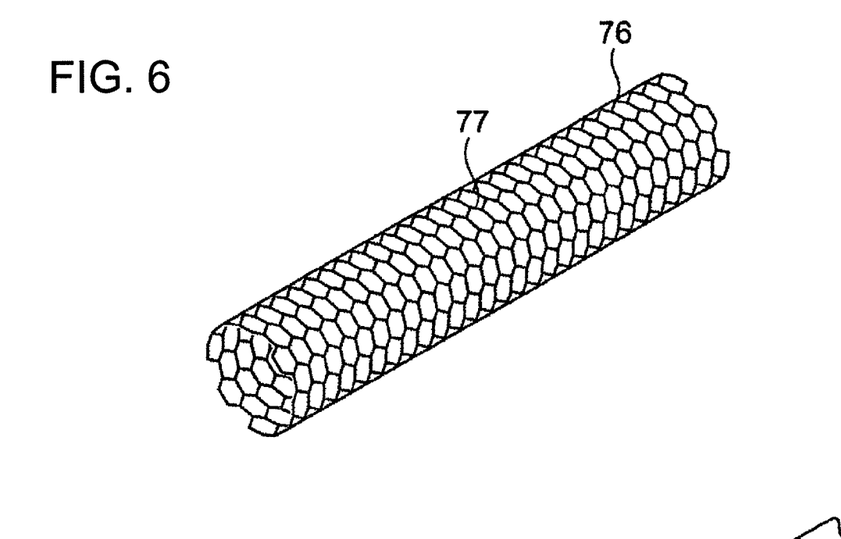
FIG. 6 is a perspective view showing the fourth modified example of a capillary tube.

In order to eliminate the process to form a hole or groove on capillary tube 48, for example, capillary tube 48 may be formed by mesh tube 76 which looks like a stent as a medical device, as shown in FIG. 6. In this case, a matching material freely goes in and out gap 54 of fixed optical fiber 33 and rotation optical fiber 53 through mesh openings 77, to avoid a change in properties of the matching material and generation of bubbles.

Figure 7:
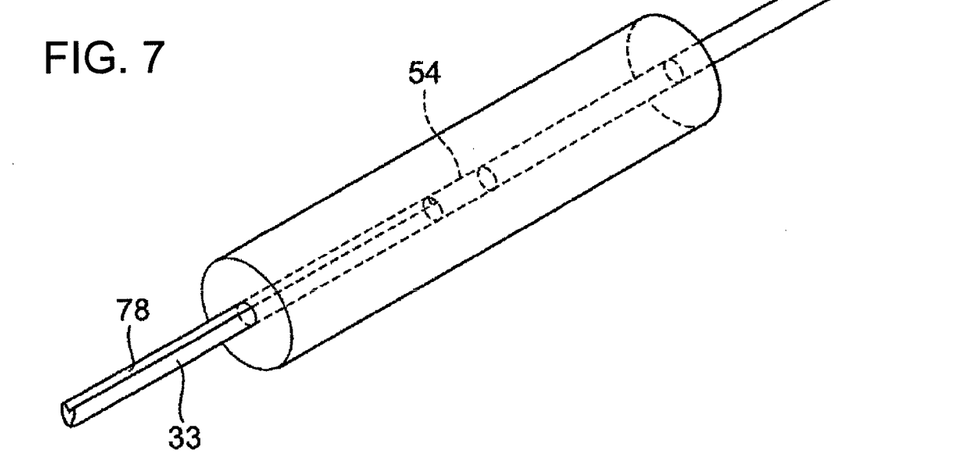
FIG. 7 is a perspective view showing the first example that a connecting section is arranged in a fixed optical fiber.
Figure 8:
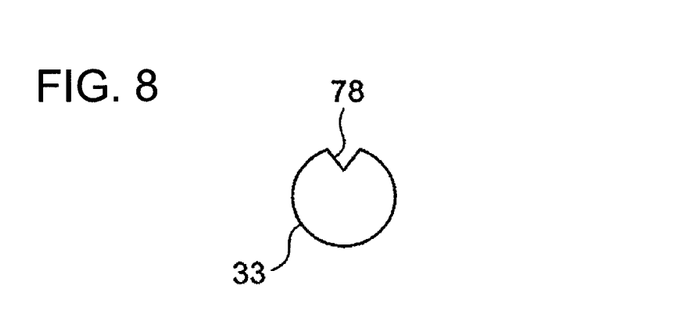
FIG. 8 is a sectional view of the fixed optical fiber shown in FIG. 7.
Figure 9:
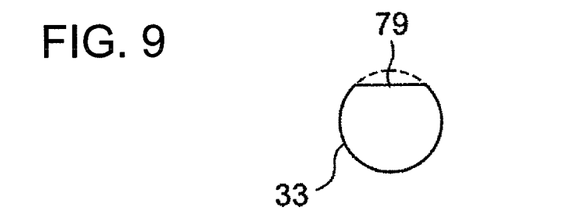
FIG. 9 is a perspective view showing the second example of a fixed optical fiber wherein a connecting section is arranged.

In place of the above method, as shown in FIGS. 7, 8 and 9, groove 78 or notch 79 may be formed in the longitudinal axis direction on the outer circumference surface of the clad of optical fiber 33 located in chamber 49 housing matching material 58, to connecting chamber 49 and gap 49 through groove 78 or notch 79.

Figure 10:
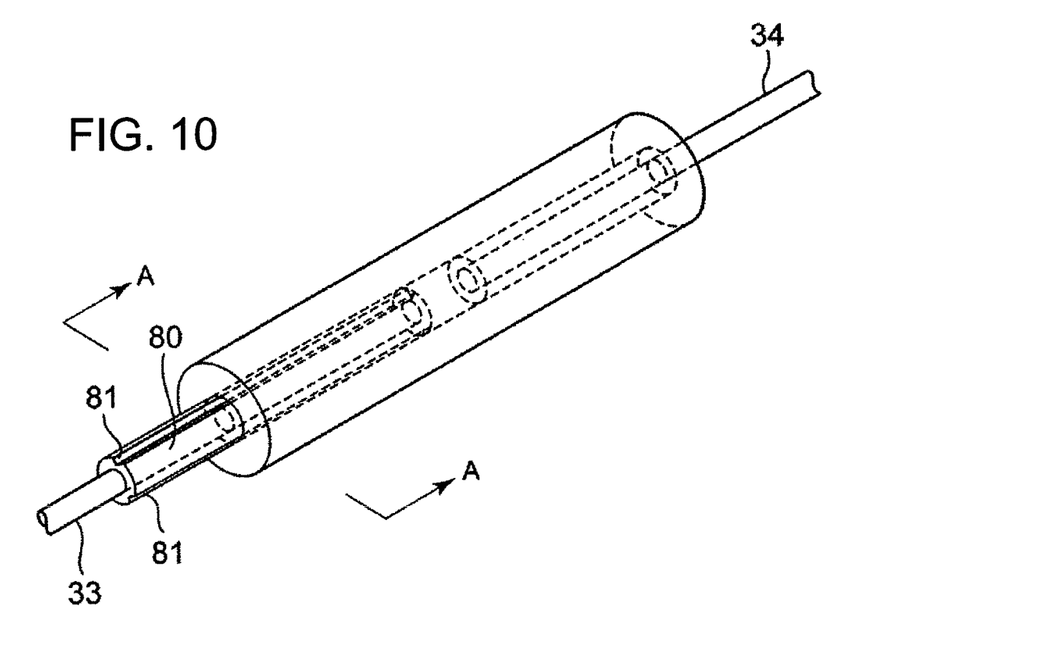
FIG. 10 is a perspective view showing the first example of a tube member where a fixed optical fiber is arranged.
Figure 11:
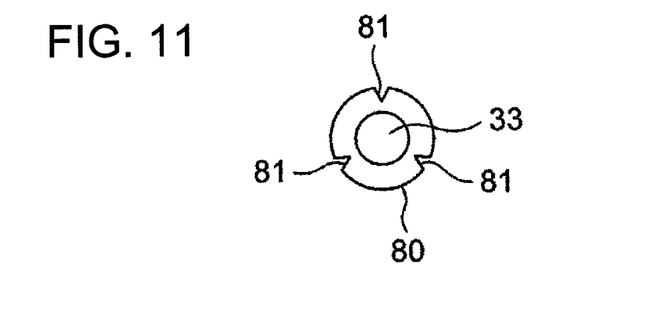
FIG. 11 is a sectional view of the tube member shown in FIG. 10.

In place of forming the groove and notch, there can be provided a astructure as shown in FIGS. 10 and 11. In the structure, tube member 80 is arranged at at least an area between the outer circumference of optical fiber 33 located in chamber 49 and capillary tube 48. Groove 81 or a notch (which is not illustrated) is formed on tube member 80 along the longitudinal direction to connect chamber 49 and gap 54. In the embodiment, tube member 80 may be fixed on optical fiber 33 or is arranged so as to freely rotate with respect to optical fiber 33.

Figure 12:
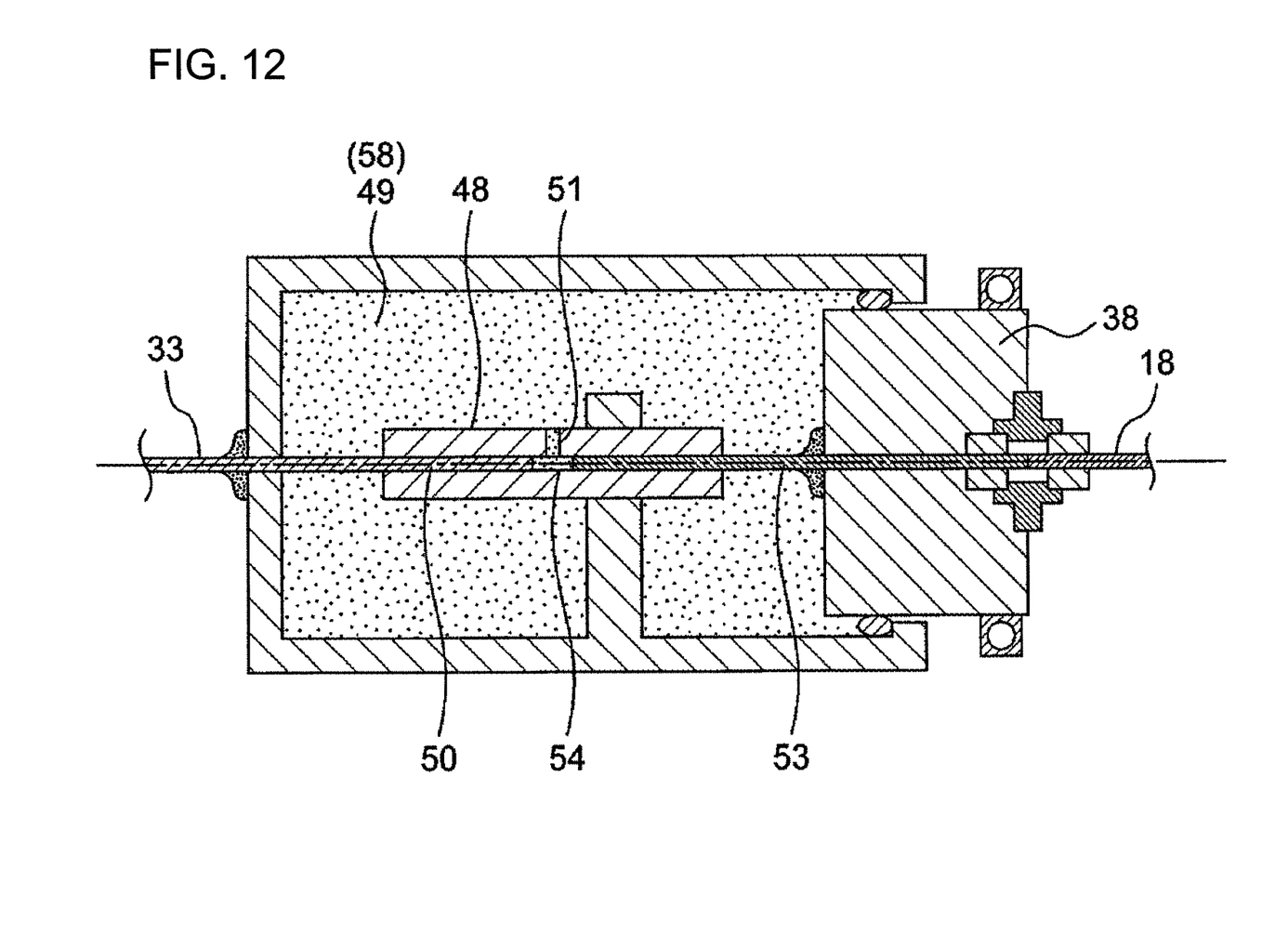
FIG. 12 is a sectional view of a modified example of an optical connector.

Further, in the above embodiment, the capillary tube is fixed on rotator 38, but may be fixed on housing (stationary section) as shown in FIG. 12. In this case, as shown in the figure, optical fiber 53 arranged between optical fiber 33 at the proximal end and optical fiber 18 at the distal end is fixed on rotator 38 and its proximal end is inserted into the distal end of cavity 50. Then, gap 54 formed between optical fibers 33 and 53 is connected with chamber 49 through connecting section 51, and matching material 58 goes in and out gap 54 corresponding to the pressure change of gap 54, to maintain the pressure in the gap to be constant.

In the above, plural modified examples are described separately. These plural modified examples can be arbitrarily combined with the other and the present invention includes such the modified examples.

The above-described optical tomorahphic imaging apparatus relating to the above embodiments is categorized in a so-called time-domain OCT, but the above various embodiments can be applied to another methods (spectrum-domain OCT, swept-domain OCT and Fourier-domain OCT) of optical tomographic imaging apparatuses.

REFERENCE SIGNS LIST

10 Optical tomographic imaging apparatus
11 Light source
13 Coupler (Optical splitter, Optical combiner)
16 Irradiation section
17 Probe
18, 33, 53 Optical fiber
19 Optical connector
21 Blood vessel (Imaging subject)
23 Optical path length adjusting section
24 Light guide
25 Lens optical system
26 Mirror
28 Interfering light detecting section
29 Image processing section
30 Control section
31 Image display section
32 Light guide tube
34 Jacket
35 Housing
36 Rotary joint
37 Stator
38 Rotator
39 Annular tube section
41 Base axis
42 Cylinder
44 Motor
45 Step section 46 Seal
47 Through hole
48 Capillary tube
49 Chamber
50 Cavity (Lumen)
51 Connecting section
52 Wall
54 Gap
55 Adopter
56 Connector
57 Adhesive
58, 71 Matching material
59 Motor rotating shaft
63 Connector
64 Distributed (Gradient) index lens
65 Rectangular prism
66 Sleeve
67 Sheath
68 Cap
69 Sealing member
70 Space
72 Clamp
73 Hole
74, 78, 81 Grooves
75 Connecting groove
76 Mesh tube
77 Mesh opening
79 Notch
80 Tube member

The invention claimed is:

1. An optical connector comprising;
a tube;
optical fibers configured to be inserted into a lumen of the tube from both sides of the tub;
a first structure configured to hold one of the optical fibers in a non-rotating condition relatively to the tube; and
a second structure configured to hold the other of the optical fibers in a rotatable condition relatively to the tube,
wherein an end of one of the optical fiber and an end of the other of the optical fiber are separated in the lumen to form a gap between the ends, and
one of the optical fibers and the other of the optical fibers are optically connected through the gap,
the optical connector further comprises:
a connecting section for connecting an exterior space of the tube and the gap, wherein
the exterior space, the gap, and the connecting section hold liquid or fluid composed of a material which can transmit light; and a structure configured to hold the liquid or the fluid on the exterior space.

2. The optical connector of claim 1,
wherein the connecting section is formed in at least one of the tube, the one of the optical fibers and the other of the optical fibers.

3. The optical connector of claim 1, wherein:
the first structure is a stator stationarily arranged so as not to rotate; and
the second structure is a rotator supported so as to be rotatable on a center axis of the tube relatively to the stator,
wherein the exterior space is formed with the stator and the rotator, and an end section of the one of the optical fiber or the other optical fiber is fixed to the rotator.

4. The optical connector of claim 3,
wherein the tube is fixed to the rotator.

5. The optical connector of claim 3,
wherein the tube is fixed to the stator.

6. The optical connector of claim 1,
wherein the connecting section is formed in a tube member arranged between at least one of the optical fibers, and the tube.

7. An optical tomographic imaging apparatus for obtaining a tomographic image of a subject by a way that light emitted from a light source is divided into irradiation light and reference light, the irradiation light is guided with an optical fiber, and interfering light of the irradiation light and the reference light is detected while the subject is irradiated with the irradiation light along a transverse cross section of the subject by rotating the optical fiber on a longitudinal axis thereof under a condition that the optical fiber is inserted to the subject,
wherein an optical fiber to be inserted to the subject is optically connected with the optical connector of claim 1, and
the irradiation light is transmitted through the optical connector and the optical fiber to be inserted to the subject.

* * * * *